United States Patent [19]

Ellis et al.

[11] Patent Number: 4,769,319

[45] Date of Patent: Sep. 6, 1988

[54] NUCLEIC ACID PROBES FOR PRENATAL SEXING

[75] Inventors: Steven B. Ellis, La Jolla; Michael M. Harpold, San Diego, both of Calif.

[73] Assignee: Salk Institute Biotechnology Industrial Associates, Inc., San Diego, Calif.

[21] Appl. No.: 739,817

[22] Filed: May 31, 1985

[51] Int. Cl.$^4$ .................. C12Q 1/68; C12N 15/00; C07H 17/00

[52] U.S. Cl. .................... 435/6; 435/172.3; 436/501; 436/814; 536/27; 935/3; 935/9; 935/63; 935/78

[58] Field of Search ................ 435/6, 172.3; 436/501, 436/814; 536/27; 935/3, 9, 63, 78

[56] References Cited

FOREIGN PATENT DOCUMENTS 8600342  1/1986  World Int. Prop. O. .

OTHER PUBLICATIONS

Nallaseth, et al., "Isolation of Recombinant Bacteriophap . . . ", Mol. Cell Genet. 190, 80–84 (1983).
Langer, P. R. et al., "Enzymatic Synthesis of Biotin-Labeled Polynucleotides . . . ", Proc. Natl. Acad. Sci. USA 78(11), 6633–6637 (Nov., 81).
Gosden, J. R. et al., "Rapid Fetal Sex Determination . . . ", The Lancet 1, 540–541, Mar. 10, 1984.
Burns, J. et al., "Sensitive System for Visualizing Biotinylated DNA . . . ", J. Clin. Pathol. 38, 1085–1092 (1985).
Vergnaud et al., Rapid and Early Determination of Sex Using Trophoblast Biopsy Specimens and Y Chromosome Specific DNA Probes, Brit. Med. Jour. 289, 73–76 (1984).
Lau et al., A Rapid Screening Test for Antenatal Sex Determination, The Lancet, Jan. 7, 1984, pp. 14–16.
Bishop et al., Single Copy DNA Sequences Specific for the Human Y Chromosome, Nature 303, 831–832 (1983).
Gosden et al., Direct Vision Chorion Biopsy and Chromosome-Specific DNA Probes for Determination of Fetal Sex in First Trimester Prenatal Diagnosis, The Lancet, Dec. 25, 1982, pp. 1416–1419.
Bostock et al., Localisation of a Male-specific DNA Fragment to a Subregion of the Human Y Chromosome, Nature 272, 324–328 (1978).
Cooke, Repeated Sequence Specific to Human Males, Nature, 262, 182–186 (1976).
Kunkel et al., Human Y-Chromosome-Specific Reiterated DNA Science 191, 1189–1190 (1976).
Streeck, A Multicopy Insertion Sequence in the Bovine Genome with Structural Homology to the Long Terminal Repeats of Retroviruses, Nature 298, 767–769 (1982).
Burk et al., Characterization and Evolution of a Single-Copy Sequence from the Human Y Chromosome, Mol. Cell. Biol. 5, 576–581 (1985).
Frommer et al., Human Satellite I Sequences Include a Male Specific 2.47 kb Tandemly Repeated Unit Containing One Alu Family Member per Repeat, Nucleic Acids Research 12, 2887–2900 (1984).
Lamar and Palmer Y-encoded, Species-specific DNA in Mice: Evidence that the Y Chromosome Exists in Two Polymorphic Forms in Inbred Strains, Cell 37, 171–177 (1984).
Tone et al., Genus Specificity and Extensive Methylation of the W-Chromosome-Specific Repetitive DNA Sequences from the Domestic Fowl, *Gallus gallus domesticus,* Chromosoma (Berlin) 89, 228–237 (1984).
Epplen et al., Base Sequence of a Cloned Snake W-Chromosome DNA Fragment and Identification of a Male-specific Putative mRNA in the Mouse, Proc. Nat'l. Acad. Sci. (USA) 79, 3798–3802 (1982).
Kunkel et al., Organization and Heterogeneity of Sequences Within a Repeating Unit of Human Y Chromosome Deoxyribonucleic Acid Biochemistry 18, 3343–3353 (1979).

*Primary Examiner*—Sidney Marantz
*Assistant Examiner*—Richard Wagner
*Attorney, Agent, or Firm*—Fitch, Even, Tabin & Flannery

[57] ABSTRACT

Nucleic acid hybridization probes are provided which have sequences complementary to sequences of segments in bovine male-specific DNA and are suitable for sexing bovine embryos at the time of embryo transfer with virtually 100% accuracy.

27 Claims, No Drawings

NUCLEIC ACID PROBES FOR PRENATAL SEXING

TECHNICAL FIELD

The present invention relates to prenatal sexing of mammals. More particularly, it relates to nucleic acid hybridization probes useful for such sexing.

BACKROUND OF THE INVENTION

The capability to determine soon after fertilization with virtually 100% accuracy the sex of mammalian embryos would provide numerous advantages in the dairy and livestock industries as well as veterinary and human medicine. The economic efficiency of livestock and dairy operations would be significantly improved by allowing gestation to continue beyond the very early stage only for embryos of the desired sex. Certain diseases, such as X-chromosone-linked diseases in humans and comparable diseases in other mammals, affect individuals of only one sex; an early, virtually certain determination of the sex of an embryo which, if carried to term, might be an individual with such a disease would provide valuable information on which to base a decision whether or not to carry the embryo to term.

In situations where, for economic or health reasons, a determination of embryo sex is indicated, it is advantageous to determine the sex as soon as possible after fertilization. Risks, to the life and health of a female carrying an embryo, of having the embryo aborted increase substantially as the period of gestation lengthens. With livestock, it is economically inefficient, both because of risks to life and health and because of reduced reproductive efficiency, for a female to carry longer than necessary an embryo that ultimately will be aborted.

With recent advances in in vitro fertilization, long-term embryo-preservation and embryo-transfer technologies, it would be feasible to avoid all risks and costs associated with pregnancy and abortion of an embryo of undesired sex, if it were possible to determine with virtual certainty the sex of an in vitro fertilized or transferred embryo prior to or at the time transfer for gestation to term is carried out.

Prior to the present invention, a sufficiently sensitive, rapid and reliable method for determining the sex of a mammalian embryo of fewer than about $10^4$ cells in three or fewer days has not been available. Thus, until the instant invention, it has not been possible to realize the many health and economic benefits of sexing embryos with virtual certainty soon after fertilization.

Using sperm, separated according to the sex chromosome they contain, to fertilize ova would accomplish the same result as embryo-sexing according to the present invention, if it were possible to routinely obtain preparations of sperm in which more then about 99% carried the sex chromosome of only one of the sexes. Currently known techniques for separating sperm are not practical for obtaining mixtures of sperm with more than about 75% harboring the same sex chromosome. Predetermining sex by segregating sperm is thus substantially less accurate than necessary to fully realize the advantages of early embryo-sexing.

Sexing can be accomplished for fetuses after several weeks of gestation by karyotyping fetal cells obtained by amniocentesis, chorion biopsy or other invasive procedures, usually followed by culturing of cells so obtained.

Human fetuses have been sexed, at 6 to 15 weeks gestational age, by nucleic acid hybridization of DNA from cells obtained from chorion or placental biopsy or embryonic fluid. In these fetal sex determinations, probes were used that correspond to DNA segments that occur about $10^3$ times in male human DNA and much more frequently in male than female human DNA. Vergnaud et al., Brit. Med. J. 289, 73–76(1984); Lau et al., The Lancet, Jan. 7, 1984, pp. 14–16; Gosden et al., The Lancet, Dec. 25, 1982, pp. 1416–1419; Bostock et al., Nature 272, 324(1978). Probes of the present invention, which are sufficiently sensitive to sex a mammal with DNA from fewer than $10^3$ of its cells, can also be used to sex fetuses. While sexing of fetuses by karyotyping or nucleic acid hybridization is virtually 100% accurate, it occurs after several weeks of gestation and involves significant risks to the fetus and mother associated with invasive procedures to obtain fetal cells. Thus, these known procedures for sexing of fetuses have serious disadvantages compared with early embryo sexing made feasible by the instant invention.

DNA segments that preferentially hybridize to male, in comparison with female, human DNA have been found. See Kunkel et al., Science 191, 1189–1190 (1976); Cooke, Nature 262, 182 (1976); Bostock et al., supra; Gosden et al., supra; and Bishop et al., Nature 303, 831 (1983). The sequences of these segments are not known. The extent to which any of these segments preferentially hybridizes to male (in comparison with female) DNA of non-human species has not been tested and, hence, remains unknown. There is no segment that is known to bind preferentially to male, in comparison with female, DNA of species of genera Bos (bovine), Capra (caprine), Equus (equine), Ovis (ovine), and Sus (porcine).

Further, there is nothing in the prior art to indicate that any DNA segments exist in mammalian male DNA that could be used to provide the basis for a nucleic acid probe to sex by nucleic acid hybridization, in fewer than about 3 days and with virtually 100% accuracy, a mammalian embryo at an early stage, at or before the time of transfer of the embryo for gestation to term.

SUMMARY OF THE INVENTION

We have discovered segments in male bovine DNA that make feasible the rapid, essentially 100% accurate sexing of bovine embryos by nucleic acid hybridization with an amount of DNA equal to the amount obtained from 4 or fewer embryonic cells. We have found nucleic acid probes which can be employed to sex bovine embryos in less than a day or two at an early stage, at or before the time embryo transfer is carried out. With the present invention, the advantages of very early and virtually certain sexing of bovine embryos can be realized.

Further, we have discovered methods for isolating, from male DNA of a mammalian species, segments which hybridize to a significantly greater extent with the DNA of the male than of the female of the species. Such segments are the basis for nucleic acid hybridization probes for sexing mammalian embryos and fetuses.

DETAILED DESCRIPTION OF INVENTION

The present invention encompasses nucleic acids which, when suitably labeled to be detectable in an hybridization system, are hybridization probes useful for sexing mammals prenatally; the probes resulting from so labeling such nucleic acids; methods of isolating and identifying such nucleic acids and probes; and methods of using the probes in prenatal sexing of mammals.

The nucleic acids of the invention, both unlabeled and labeled (i.e., probes), can be single-stranded or double-stranded DNA or RNA or hybrids between DNA and RNA. The sequence of a labeled nucleic acid is the sequence the nucleic acid would have if each labeled nucleotide (i.e., deoxyribonucleotide or ribonucleotide) in the sequence were replaced with the corresponding unlabeled nucleotide. Thus, if a DNA is labeled with biotin linked to the 5-position of deoxyuridylate residues, the sequence of the labeled DNA is the same as that of the DNA wherein all of the biotin-labeled deoxyuridylates are replaced with thymidylates. The sequences of a DNA and a RNA are the same if every deoxyribonucleotide, except thymidylate, in the DNA is replaced with the corresponding ribonucleotide in the RNA and every thymidylate in the DNA is replaced with uridylate in the RNA.

The essential feature of the nucleic acids of the invention, both unlabeled and labeled, is that, when in single-stranded form, they hybridize to a significantly greater extent with total male DNA than total female DNA of a bovine species, when the hybridizations are carried out under substantially the same conditions. By hybridization; to a "significantly greater extent" is meant that the quantity of nucleic acid that hybridizes is, with a probability greater than 0.99, larger.

The preferred probes according to the invention will not hybridize detectably to total female bovine DNA in an hybridization under stringent conditions over an hybridization period during which detectable hybridization with total male bovine DNA does occur.

Preferably the probes according to the invention will be employed in hybridizations under stringent conditions with total (i.e., chromosomal) DNA derived from cells of an embryo or fetus of the species being tested. Stringent conditions and total DNA are defined in more detail below.

Preferred nucleic acids and probes according to the invention, derived from bovine male DNA, are described in detail in the following examples.

As is well known in the nucleic acid hybridization probe art, nucleic acids with different sequences may, under the same conditions, hybridize detectably to the same "target" nucleic acid. Two nucleic acids hybridize detectably, under stringent conditions over a sufficiently long hybridization period, because one ("probe") comprises a segment of at least about 10 nucleotides ("probing segment") in a sequence which is complementary or nearly complementary to the sequence of at least one segment ("target segment") in the other ("target"). The physical basis for hybridization is base-pairing between these complementary or nearly complementary segments. If the time during which hybridization is allowed to occur is held constant, at a value during which, under preselected stringency conditions, two nucleic acids with exactly complementary base-pairing segments hybridize detectably to each other, increasing departures from exact complementarity can be introduced into the base-pairing segments, but base-pairing will nonetheless occur to an extent sufficient to make hybridization detectable, as the base-pairing segments of two nucleic acids become larger and as conditions of the hybridization become less stringent. Further, segments outside the probing segment(s) of a probe nucleic acid (that hybridizes to a particular target nucleic acid) can be changed completely in sequence without substantially diminishing the extent of hybridization between the probe and its target, if the change does not introduce a probing segment complementary (or nearly complementary) to a target segment in a different target present in samples to be probed. Even if no such new probing segment is introduced, if the segments outside the probing segment are changed substantially in length, the rate of hybridization might be altered. Two single-stranded nucleic acid segments have "substantially the same sequence," within the meaning of the present specification, if (a) both form a base-paired duplex with the same segment, and (b) the melting temperatures of said two duplexes in a solution of 0.5×SSPE differ by less than 10° C. If the segments being compared have the same number of bases, they will typically differ in their sequences at fewer than 1 base in 10 to have "substantially the same sequence". Two double-stranded nucleic acid segments have "substantially the same sequence" if either strand of one of the segments has "substantially the same sequence" as one strand of the other of the segments.

Methods for determining melting temperatures of nucleic acid duplexes are well known. See, e.g., Meinkoth and Wahl, Anal. Biochem. 138, 267–284(1984) and references cited therein.

To be used as an hybridization probe in accordance with the present invention, a nucleic acid according to the invention must be rendered detectable by being labeled. Preferably the nucleic acids of the invention are detectably labeled with $^{32}P$. Other radioactive labels, such as $^3H$ or $^{14}C$, may also be employed.

Detectably labeling a DNA of the invention with a radioactive isotope is conveniently accomplished by nick-translating a sample of the DNA in the presence of one or more deoxynucleoside-5-triphosphates which are themselves labeled with the isotope.

Non-radioactive labels known in the art can also be employed, provided they render the probes according to the invention sufficiently sensitive for sexing during the time available (for culturing cells, if necessary; extracting DNA; and hybridization assay) with DNA from the number of cells available as source of DNA. Clearly, a probe to be used to determine, within two days, the sex of an embryo with DNA from four cells will need to be more sensitive than a probe to be used for determining, within 30 days, the sex of a fetus with DNA from $10^4$ cells.

A nucleic acid according to the invention can be made detectable by being chemically labeled. One method of chemically detectably labeling such a nucleic acid that is a DNA is to nick-translate the nucleic acid in the presence of deoxyuridylate biotinylated at the 5-position of the uracil moiety to replace thymidylate residues. The resulting probe will include the biotinylated uridylate in place of thymidylate residues and can be detected (via the biotin moieties) by any of a number of commercially available detection systems based on binding of streptavidin to the biotin. See Langer et al., Proc. Natl. Acad. Sci. U.S.A. 78, 6633–6637(1981); Langer-Safer et al., Proc. Natl. Acad. Sci. U.S.A. 79, 4381–4385(1982); Singer and Ward, Proc. Natl. Acad. Sci. U.S.A. 79, 7331–7335(1982); Leary et al., Proc. Natl. Acad. Sci. U.S.A. 80, 4045–4049(1983); Brigati et al., Virology 126, 32–50(1983). The above-mentioned commercially available detection systems can be obtained from, e.g., Enzo Biochemicals, Inc., New York, N.Y., U.S.A. and Bethesda Research Laboratories, Inc., Gaithersburg, Md., U.S.A.

Making and using the nucleic acids and probes of the invention are described in detail in the following examples.

To make a nucleic acid according to the invention, a genomic library (which will usually be a partial genomic library) of the male of the species of interest is prepared, screened with a male specific DNA preparation (also referred to as "male specific probe preparation") of DNA from the male of the species to identify clones (or colonies which comprise clones) which include DNA with which DNA of the male-specific probe preparation hybridizes, and then screening the clones (or colonies) so identified for clones which include DNA which hybridizes to a greater extent with male DNA than with female DNA. Preferably the clones identified in the second screening are further screened to identify the clones containing DNA which hybridizes detectably within 20 hours with total male DNA but not total female DNA of the species in an assay conducted under stringent conditions, with the DNA of the clones labeled radioactively to a high specific activity (approximately $4 \times 10^8$ CPM/$\mu$g).

The clones identified in the screening, wherein the extent of hybridization with male DNA and female DNA is compared, harbor cloned DNA, usually in the form of plasmid or phage vectors, which are nucleic acids according to the invention. Each of these cloned DNAs, in turn, includes a segment of genomic DNA, from the male of the species of interest, which is an element of the genomic library or partial library harbored in the set of screened clones and is also a nucleic acid according to the invention.

In preparing a male genomic or partial genomic library, for screening for clones with nucleic acid of the invention, digestion of male chromosomal DNA with any one or more restriction endonucleases with a recognition sequence of four, five or six base pairs (bp), or random fragmentation of male chromosomal DNA to an average size of about 1,000 bp, by sonication or digestion with DNaseI, is suitable. For bovine male DNA, digestion with RsaI alone or both RsaI and EcoRI together are preferred. If a partial genomic library is prepared for screening, it will preferably include DNA fragments between about 200 bp and about 10,000 bp in length, more preferably 2500 bp to 7,000 bp.

Any cloning vector, such as a lambda phage or cosmid vector or any of various plasmid vectors, that is suitable for preparing a genomic or partial genomic library, can be employed for making the library of male DNA. Typically such vectors will be less than about 50 kilobase pairs (kbp) in size. Plasmid pBR322, cleaved at the single PstI site, and tailed with dGTP, is conveniently employed, with dCTP-tailed chromosomal DNA fragments, as described in the examples below.

The male specific DNA preparation ("male specific probe preparation") used in various screening steps is prepared by solution hybridization of randomly fragmented, labeled total male DNA, with an average fragment size of about 10 to about 1,000, preferably about 400 to about 800, nucleotides with a 10-fold to $10^5$-fold, preferably about $10^3$-fold, mass excess of randomly fragmented total female DNA, with an average fragment size of about 10 to about 1,000, preferably about 400 to about 800, nucleotides. The hybridization is carried out for 20-30 hours, preferably about 24 hours, at stringency conditions defined by: a temperature of 37° C. to 50° C., preferably about 42° C., in 40% (v/v)-60% (v/v), preferably about 50% (v/v) deionized formamide; $0.7\times$ to $1.3\times$, preferably about $1.0\times$ Denhardt's solution; $4\times$ to $6\times$ preferably about $5\times$ SSPE, 7% (w/v) to 13% (w/v), preferably about 10% (w/v) dextran sulphate; and 400 $\mu$g/ml to 600 $\mu$g/ml, preferably about 500 $\mu$g/ml heparin. The concentration of labeled male DNA is preferably about 1 $\mu$g/ml. After the solution hybridization, the DNA solution is preferably filtered through a material such as nitrocellulose. A male specific probe preparation is a solution of DNA fragments essentially all of which include at least one segment of longer than 10 nucleotides which occurs in total male, but not in total female, DNA of the involved species. DNA can be randomly fragmented by known methods, including sonication and digestion with DNaseI; and the average size of fragments can be estimated with sufficient accuracy for purposes of the present invention by standard DNA sizing techniques (e.g., comparing migration distance of fragmented DNA during electrophoresis on an agarose gel with fragments of known size). The randomly fragmented, labeled total male DNA is conveniently prepared by nick-translation of total male DNA with alpha-$^{32}$P-labeled nucleoside triphosphates, following standard nick-translation procedures, to obtain DNA fragments of the desired average size and labeled to the desired specific activity. See Maniatis et al., Molecular Cloning: A Laboratory Manual, Cold Spring Harbor Laboratory Press., Cold Spring Harbor, N.Y. (1982); pp. 109-112. The preparation of total male DNA and total female DNA is described in Example I below. A preferred nick-translation procedure is described in Example II.

The screening of genomic library with the male specific probe preparation is preferably carried out on a solid support, such as nitrocellulose, which has been prehybridized first with DNA unrelated to that of the species of interest, such as randomly fragmented herring sperm DNA, herring testes DNA, or salmon testes DNA or randomly cleaved tRNA (homochromatography mix, described by Jay et al., Nucl. Acids Res. 1, 331-354 (1974)), and then randomly fragmented, single-stranded total female DNA of the involved species, with a random fragment size of about 10 to about 1,000, preferably about 400 to about 800 nucleotides.

Optionally, prior to preparation of the genomic library, digests of male chromosomal DNA and female chromosomal DNA with one or more restriction endonucleases can be probed by Southern hybridization using the male specific probe preparation to attempt to identify digestion procedures to produce, as well as size ranges of, male DNA fragments for a partial male genomic library that is likely to contain nucleic acid according to the invention. An example of such an optional procedure is provided in Example II below. If DNA at a position in such a Southern blot of male DNA hybridizes more strongly with DNA of the male specific probe preparation than DNA at the corresponding position in the blot of female DNA hybridized with the same male specific probe preparation, then a library of male DNA of size corresponding to the position is likely to contain nucleic acid of the invention.

The second and third screening steps, to pick, from clones identified in the first screen, those that include DNA that not only hybridizes to male but hybridizes to a greater extent with male than female DNA, are carried out generally as outlined in the following examples. The second step entails generally probing DNA in two replicas of the clones that were identified in the first step as possibly containing male-specific DNA. One replica is probed with a male specific probe preparation made in essentially the same way as that used in the first screening step. The other replica is probed with a preparation of labeled, randomly fragmented female DNA, with an average fragment size approximately the same as that of the DNA in the male specific preparation and prepared conveniently by nick-translation with one or more alpha-$^{32}$P-labeled nucleoside triphosphates and otherwise in the same way as the male specific probe preparation but without solution pre-hybridization with female DNA. The two replicas are probed under comparable conditions so that clones with DNA that hybridizes to a greater extent with male than female DNA can be identified by simply comparing the intensity of signal from each clone on the replica hybridized with labeled male-specific probe, with the intensity of signal from the corresponding clone on the replica hybridized with labeled female-specific probe.

The third step entails screening the cloned male genomic DNA identified in the second step for ability to hybridize under stringent conditions to a significantly greater extent with total male than with total female DNA. The third step is intended to identify clones (i.e., cloned DNAs) that clearly detectably hybridize with total male DNA and do not detectably hybridize with total female DNA of the species of interest over the time period of hybridization and detection. Such clones are "male specific". They are especially useful as the basis for nucleic acid hybridization probes for prenatal sexing of the involved mammalian species.

In a preferred procedure, the third screening step involves using nick-translated vector DNA from each of the clones isolated in the second screening step as a probe of a Southern digest of both male and female total DNA and identifying the clones containing DNA that hybridizes detectably with the male but not the female DNA.

Application of probes of the invention to sex mammalian embryos is described in the Examples.

A method for determining whether a nucleic acid of the invention is suitable to provide probe of the invention for sexing a mammal prenatally with chromosomal DNA from fewer than a preselected number of embryonic or fetal cells is provided in Example VI below. The method comprises simply carrying out hybridizations, with probe prepared from the nucleic acid, with increasing dilutions of total male and total female DNAs and determining the smallest quantity of DNA at which hybridization with the male DNA is distinguishable from that with the female DNA when hybridization and detection are conducted over time periods deemed to be suitable (e.g., comparable to periods to be employed with the probes in commercial applications).

Generally, a nucleic acid according to the invention is labeled prior to hybridization with DNA from cells of the embryo or fetus to be sexed. Particularly with embryo sexing, where the amount of embryonic DNA available as "target DNA" for hybridization is generally quite small, radioactive labeling of nucleic acid of the invention to high specific activity is prefered; a convenient method of accomplishing such labeling is nick-translation of nucleic acid of the invention with deoxynucleoside triphosphates labeled with $^{32}$P to a high specific activity (e.g., 3200 Ci/mmole). The preferred procedure for carrying out this nick-translation is provided in Example II.

It will be recognized that RNA probes according to the invention could be prepared by synthesis of $^{32}$P-labeled RNA with an in vitro synthesizing system employing alpha-$^{32}$P-labeled (ribo) nucleoside triphosphates with DNA-dependent RNA-polymerase-catalysis and DNA according to the invention as template.

The total (i.e., chromosomal) DNA is isolated from cells of the fetus or embryo to be sexed and, preferably, affixed to a solid support such as nitrocellulose. The nitrocellulose with DNA fixed is then typically prehybridized, preferably under stringent conditions, to minimize non-specific binding of probe. Then the DNA on the (prehybridized) nitrocellulose is hybridized, also preferably under stringent conditions over a period of about 17 hours, with labeled probe according to the invention. Then, after post hybridization washing, also preferably under stringent conditions, the support is treated appropriately to observe any signal associated with detectable label on probe that might have hybridized and thereby, preferably by comparison with signals from controls, ascertain whether significant hybridization between probe and fetal or embryonic DNA occured. Procedures that may be employed in detecting signal from hybridized probe are well known in the art; for $^{32}$P-labeled probe, preferred autoradiographic procedures are provided in the Examples. In a preferred application of the invention, hybridization of labeled probe with DNA derived from an approximately known number of cells of an embryo or fetus will be conducted in parallel with control hybridizations, one with DNA derived from approximately the same number of cells from a known female of the same species and the other with DNA from approximately the same number of cells from a known male of the same species as that of the embryo or fetus. The test and control hybridizations will be carried out following essentially the same procedures and employing essentially the same conditions. The signal from probe hybridized with embryonic or fetal DNA being tested can then be compared with the signals from probe hybridized with the known male and female DNA standards and a determination of fetal or embryonic sex more easily and accurately made. Significant hybridization of probe with embryonic or fetal DNA being tested is indicated by a signal with that DNA, that is significantly above the signal from the hybridization with known female DNA, and significant hybridization is confirmed if the signal from hybridization with embryonic or fetal test DNA is approximately the same as that from the hybridization with known male DNA. The absence of significant hybridization is indicated by signal with embryonic or fetal test DNA that is approximately the same as the signal with known female DNA and is confirmed by the signal with embryonic or fetal test DNA being significantly less than that with known male DNA. Significant hybridization of probe with DNA from an embryo or fetus indicates the embryo or fetus is a male. The absence of significant hybridization indicates the embryo or fetus is a female.

The most preferred probes according to the invention are those which hybridize appreciably only with male DNA. With such probes, single negative control hybridization (with DNA derived from a female of the species) run in parallel with hybridization of DNA from the fetus or embryo being sexed will generally be sufficient for ease and accuracy in sexing.

As will be apparent to those of skill, once a nucleic acid of the invention that consists of double-stranded DNA is prepared, numerous techniques are available to make a corresponding single-stranded DNA (simply by strand separation), a corresponding single-stranded or double-stranded RNA, and corresponding DNA-RNA hybrids.

The sequence of a nucleic acid of the invention can be determined, using, for example, known Maxam-Gilbert techniques. Then, in addition to various enzymatic in vitro and in vivo methods for making large quantities of the nucleic acid, automated, in vitro, stepwise synthesis techniques for making the nucleic acid, labeled as well as unlabeled, can be employed.

Those of skill will also recognize that various components necessary for carrying out prenatal sexing of a mammal in accordance with the instant invention can be assembled into kits to facilitate sexing on site in veterinarians' offices, or on dairy farms, cattle ranches, and the like.

The invention is now described in greater detail in the following examples:

EXAMPLE I

The procedure for the preparation of bovine chromosomal DNA is described in this Example. DNA prepared according to this Example from male bovine tissue is also referred to in the specification as "total (bovine) male DNA." Similarly, DNA prepared according to the Example from bovine female tissue is also referred to as "total (bovine) female DNA."

Male Holstein bovine liver and female Hereford bovine liver were obtained from the Talone Packing Company, Escondido, Calif., U.S.A. The tissue from each sex was processed separately, but by the same procedure, to yield a preparation of male bovine chromosomal DNA (also referred to herein as "total male bovine DNA" or "male bovine DNA") and a preparation of female bovine chromosomal DNA (also referred to herein as "total female bovine DNA" or "female bovine DNA").

Liver tissue (40 g) was powdered in a Waring Blender in the presence of liquid nitrogen. The liquid nitrogen was allowed to evaporate, and the powdered tissue was then transferred to a beaker containing 400 ml of PK buffer. Immediately thereafter, proteinase K (20 mg) in 1 ml of H$_2$O was added to the tissue/buffer mixture, which was then vigorously mixed and allowed to incubate at room temperature (20° C. to 30° C.) for 30 minutes. After the incubation, an equal volume of PCIA was added to the preparation and the entire contents were then mixed vigorously. The lower organic phase and the upper aqueous phase were then separated by centrifugation, and the organic phase was discarded. An equal volume of CIA was added to the aqueous phase and the contents were vigorously mixed. The two phases were then separated by centrifugation. The organic phase was discarded, and NaCl was added to the aqueous phase, adjusting it to 0.25M NaCl. Two volumes of ice-cold 95% ethanol were then gently layered onto the aqueous phase. The high molecular weight chromosomal DNA that precipitates was carefully spooled on to a pipet and transferred to a centrifuge tube. TE-buffer (40 ml) was added to the centrifuge tube, and the DNA was resuspended by shaking at 42° C. for 16 hours. Ribonuclease A (RNase A) was dissolved to 10 mg/ml in 10 mM Tris.Cl (pH 7.5) and 15 mM NaCl, and the resulting solution was heated to 100° C. for 15 minutes and then allowed to cool slowly to room temperature; aliquots of this preparation (referred to herein as "heat-treated RNase A") are stored at −20° C. (See Maniatis et al., supra, at page 451.) Heat-treated RNase A was added to DNA suspension at a final concentration of 50 μg RNase A/ml and the suspension was then incubated at room temperature for 30 minutes. Thereafter, the suspension was extracted with PCIA and then CIA as described above in this Example. The aqueous phase which was obtained was divided into eight tubes, each containing 30 g cesium chloride and 20 mg ethidium bromide. Each tube was adjusted to a final volume of 39.5 ml with TE-buffer. The tubes were centrifuged in a Beckman VTi-50 (Vertical Tube Rotor, maximum radius 8.66 cm) (Beckman Instruments, Inc., Fullerton, Calif. U.S.A.) at 49,000 rpm (approximately 215,000×g) for 18 hours. The DNA bands, which formed in the resulting cesium chloride gradients, were collected into a single centrifuge bottle, and the ethidium bromide was removed by extracting the DNA solution four times with an equal volume of TE-saturated n-butanol. DNA was precipitated by adding two volumes of 95% ethanol and holding at −20° C. overnight. The ethanol-precipitated DNA was then collected by centrifugation, resuspended in TE-buffer, and NaCl was then added to a final concentration of 0.25M. The DNA was again ethanol precipitated and collected by centrifugation. (The DNA precipitation procedure of adjusting the NaCl concentration to 0.25M, adding 2 volumes of 95% ethanol, holding the resulting solution at −20° C. for more than 12 hours or at 70° C. for 30 minutes, and collecting the DNA by centrifugation is referred to throughout this specification as "ethanol precipitation.") The DNA was finally resuspended in TE-buffer and the concentration determined by UV absorbance at 260 nm, assuming that an O.D. of 1 corresponded to a DNA concentration of 50 μg/ml. The ratio of absorbance at 260 nm to that at 280 nm was 1.8, indicating that the DNA was not significantly contaminated. (See Maniatis et al., supra, at page 468.) Typically, 1 g of tissue yielded 1 mg of DNA.

EXAMPLE II

The establishment of hybridization conditions for the visualization of male-specific bands in Southern hybridization assays (E. Southern, J. Mol. Biol., 98, 503 (1975)) on bovine male and female DNA, the identification of male-specific bands found in such assays, a male-specific probe preparation, and the nick-translation procedure employed in all nick-translations described in these examples are described in this Example.

Bovine male and female DNA (10 μg each), prepared as described in Example I, were digested in separate reactions with RsaI, according to the manufacturer's instructions. The digested DNA was precipitated directly from the reaction mix by adjusting the NaCl concentration to 0.25M and then ethanol precipitating. The precipitated DNA was collected by centrifugation and resuspended in TE-buffer. The male and female DNA samples were electrophoresed using a standard procedure in parallel lanes through a 1% TBE agarose gel. (See Maniatis et al., supra, at pp. 153–163.)

Using a standard method, the RsaI-digested fragments from each lane were transferred to a nitrocellulose filter prepared for Southern hybridization. (See Maniatis et al., supra, at pp. 383-389.) Subsequent treatment of the filter was as follows:

Prehybridization of the filter was performed in two steps: First, the filter was prehybridized with sheared herring sperm DNA and, second, the filter was prehybridized with sonicated bovine female DNA. (All procedures in this and the other Examples which involve herring sperm DNA could be carried out as well with other non-mammalian DNAs such as from herring testes or salmon testes.)

Herring sperm DNA was sheared by sonication to approximately 500 base-pairs (bp) using a Sonifier 350 (Branslon Sonic Power Co., Danbury, Conn. U.S.A.). This sheared DNA was denatured by boiling for 7 minutes and then diluted to 200 µg/ml final concentration in prehybridization buffer, which consists of 50% (v/v) deionized formamide, 5× Denhardt's solution, 5× SSPE, 0.2% (w/v) sodium dodecylsulfate (SDS), and 50 µg/ml heparin. The nitrocellulose filter with the bound male or female DNA was then placed in this prehybridization buffer and incubated at 42° C. for 5 hours. After the incubation, the filter was removed from the buffer and washed briefly in 5× SSPE.

In the second prehybridization step, the filter was prehybridized in the presence of sonicated total bovine female DNA. The bovine female DNA, prepared as described in Example I, was resuspended in TE-buffer, and sonicated in the same manner as described above for the herring sperm DNA. The bovine female DNA prehybridization buffer consisted of 50% (v/v) deionized formamide, 5× SSPE, 2× Denhardt's solution, 10% (w/v) dextran sulphate, 100 µg/ml sheared herring sperm DNA, 500 µg/ml heparin, 0.2% (w/v) SDS, and 500 µg/ml sonicated bovine female DNA. In preparing the female DNA prehybridization buffer, the formamide, sheared herring sperm DNA and sonicated bovine female DNA were combined together and placed in a boiling water bath for 5 minutes. The remaining reagents were then added to the heated mixture and then combined with the nitrocellulose filter. This prehybridization was carried out over 27 hours at 42° C.

1 µg of total male bovine DNA, prepared as in Example I, was nick-translated to a specific activity of $5 \times 10^8$ CPM/µg, with an average size of about 600 to 1000 bp in the nick-translated product, as follows:

1 µg of the male bovine DNA was mixed with 15 µl 10× nick-translation buffer, 15 µl of 10× dNTP mix, 10 µl of DNase stock, 10 µl E. coli DNA polymerase I (2 units/µl), and enough $H_2O$ to bring the solution to 100 µl. Finally, 50 µl of alpha-$^{32}$P-labeled dCTP (3.1 micromolar, labeled to 3200 Curies/mmole, in 0.01M tricine (i.e. N-tris[hydroxymethyl]methyl glycine) buffer, pH 7.6, catalog No. NEG-D13H, New England Nuclear, Inc., Boston, Mass., U.S.A.) was mixed with the solution and the resulting solution was incubated at 14° C. for 2 hours. After the two hours, the reaction was stopped by the addition of 5 µl of a solution of 0.5M EDTA and 2.5 µl of a solution of 20% (w/v) SDS. 1M NaOH (68.5 µl) was added to the solution to bring it to a final concentration of 0.3M NaOH. This nick-translated DNA solution was placed in a boiling $H_2O$ bath for 3 minutes and then chromatographed on a 5 ml Sephadex G-50 column in TE-buffer to separate the nick-translated DNA from unincorporated deoxynucleoside triphosphates.

For a discussion of factors affecting nick-translations, see Maniatis et al., supra, at pp. 109-111.

The nick-translated male bovine DNA (approximately 1 µg) was combined in TE-buffer with 1 mg of sonicated female bovine DNA, average fragment size 500 bp, prepared as described above, and the combined DNAs were ethanol precipitated and resuspended in 500 µl of deionized formamide. The DNA suspension was then placed in a boiling water bath for 3 minutes, and then transferred to 65° C. for 5 minutes. The resulting DNA solution was brought to a final volume of 1 ml consisting of, in addition to the DNA, 50% (v/v) deionized formamide, 1× Denhardt's solution, 5× SSPE, 10% (w/v) dextran sulfate, and 500 µg heparin, and then placed at 42° C. for 24 hours. Following the incubation, the highly concentrated DNA solution was filtered through nitrocellulose in a Sterifil Aseptic System, 47 mm Apparatus (Millipore Corp., Bedford, Mass., U.S.A.), under the assumption that labeled, non-specifically binding components would thereby be removed, and the filtrate was added directly to the prehybridization solution containing the prehybridized nitrocellulose filter.

The solution-prehybridization of the nick-translated male DNA generated a predominantly male-specific probe (referred to in the specification as "male specific probe preparation".) When this male-specific probe preparation was filtered through the nitrocellulose (resulting in a changed male specific probe preparation) and added to the prehybridized nitrocellulose filter, the hybridization with DNA on the filter was initiated. The concentration of nick-translated probe in the filtered solution used for hybridization was $5.0 \times 10^7$ CPM/ml (specific activity was $5.0 \times 10^8$ CPM/µg), and the hybridization was carried out at 42° C. for 48 hours. After hybridization, the filter was removed from the hybridization solution and washed in 0.2× SSPE, 0.2% (w/v) SDS briefly (to eliminate formamide from the filter) at room temperature. The filter was then washed at 65° C. for 10 minutes in the same buffer, and finally washed 2 times in 0.1× SSPE, 0.1% (w/v) SDS at 65° C. for 10 minutes each wash.

Following standard procedures, Kodak X-Omat AR x-ray film was exposed with the washed filter. (See Maniatis et al., supra, at pp. 470-471.) Exposure was for 3.5 hours with an intensifying screen.

Two male-specific bands were found, identified by their appearance in the male bovine DNA blot and the absence of corresponding bands in the female bovine DNA blot. One band, which corresponds to DNA of approximately 5 to 6 kbp (kilobase pairs), was quite strong, and appeared reproducibly when the procedures described above were repeated. The other band, which corresponds to DNA of approximately 1.6 kbp, was weak and is not observed reproducibly. The 5-6 kbp band is referred to in this specification as the "5-6 kbp RsaI fragment of male Holstein DNA."

Estimates of sizes of DNA's described in the present specification were made by a standard sizing method well known in the art, e.g., by comparing the distance the DNA's of interest migrate during electrophoresis in agarose gels with migration distances under comparable conditions of DNA's liberated by HindIII-digestion of lambda phage DNA and HaeIII-digestion of PhiX174 phage DNA.

The procedures of this Example were repeated with bovine DNA digested with both EcoRI and RsaI and then again with bovine DNA digested with only EcoRI. The results showed that the 5-6 kbp RsaI fragment includes at least one EcoRI site, as an approximately 4 kbp, strongly hybridizing male-specific fragment occurred in the EcoRI-RsaI digest in place of the 5–6 kbp fragment in the RsaI digest. Under the conditions used in the procedure it was not possible to locate any male-specific bands in the digest with EcoRI alone; it can be concluded nonetheless that the approximately 4 kbp male-specific fragment identified in the EcoRI-RsaI digest is bounded by an EcoRI site and an RsaI site. This 4 kbp fragment is referred to in this specification as "the 4 kbp RsaI-EcoRI fragment of male Holstein DNA."

EXAMPLE III

In this Example, construction of a bovine male partial genomic library is described.

Total male bovine DNA (100 µg), prepared as described in Example I, was digested with RsaI, followed by EcoRI, according to the manufacturer's instructions. Following the digestion, the DNA was ethanol precipitated directly from the digestion solution. The digested DNA was resuspended in TE-buffer and electrophoresed in a 0.8% TBE agarose gel as described in Example II. The 2,500–6,000 bp DNA fraction was isolated by electroelution into $0.5 \times$ TBE buffer according to a standard method (see Maniatis et al., supra, at pp. 164–165) and purified by ion exchange chromatography through an Elutip-d column according to the manufacturer's instructions. The DNA was ethanol-precipitated and resuspended in 8 µl $H_2O$. Approximately 10 dCMP residues were added to each 3'-hydroxy-terminus of this population of DNA fragments in a 50 µl reaction mixture consisting of 0.0075 nmoles dCTP (alpha-$^{32}$P-labeled)(800 curies/mmole), 31.5 pmoles dCTP, 10 µl $5 \times$ terminal transferase buffer, 21 units terminal transferase, and $H_2O$ to adjust to 50 µl. The reaction mixture was incubated at 37° C. for 30 minutes and then terminated by the addition of 2 µl of 0.5M EDTA, pH 8.0. The dCMP-tailed DNA mixture was then extracted with PCIA followed by CIA as described in Example I. The aqueous phase was chromatographed through a 1.5 ml Bio Gel P.60 column in TE-buffer, to separate unincorporated deoxynucleoside triphosphates from the mixture, and the dCMP-tailed high molecular weight peak was collected in a microfuge tube. Thereafter, the volume was reduced to 50 µl by extracting with n-butanol, and the DNA was ethanol-precipitated. The dCMP-tailed DNA was then resuspended in 2.5 µl TE-buffer. The dCMP-tailed DNA was annealed to 250 ng of dGMP-tailed pBR322 in 50 µl of buffer consisting of 10 mM Tris (pH 7.4), 100 mM NaCl, and 1 mM EDTA. The reaction was carried out at 65° C. for 3 minutes, then at 42° C. for 2 hours, and finally the solution was allowed to cool slowly to room temperature.

The constructed plasmid library, thus obtained, was added to 200 µl of competent *E. coli* LE392, prepared as described below, and the bacteria were transformed by incubating the mixture on ice for 10 minutes, then at 37° C. for 5 minutes and finally on ice for 10 minutes. The transformed bacteria were then diluted with 250 µl of $2 \times$ Luria Broth (LB) and incubated at 37° C. for 45 minutes. The bacteria were plated onto $2 \times$ LB agar plates containing 15 µg/ml tetracycline and incubated at 37° C. The resulting library consisted of 4,000 colonies.

Any strain of *E.-coli* suitable for cloning vectors with a ColE1 replication system, such as pBR322, could be used in place of *E. coli* LE392 in all steps described in the present specification in which *E. coli* LE392 was used. Many such strains are known and readily available to the skilled.

*E. coli* LE392 is available to the art. Its genotype is F−, hsdR514($r_K^-$,$m_K^-$), supE44, supF58, lacY1 or delta(lacIZY)6, galK2, galT22, metB1, trpR55, lambda−. (See Maniatis et al., supra, at pp. 504.)

*E. coli* LE392 were made competent as follows: An overnight culture, grown in $2 \times$ LB, was diluted with 39 volumes of $2 \times$ LB and grown to an $A_{600}$ of 0.3; the volume of this resulting culture is the "original culture volume". The culture was chilled on ice for 10 minutes and the bacteria were then collected by centrifugation. The resulting bacterial pellet was resuspended with cold 0.1M $CaCl_2$ in $0.4 \times$ the original culture volume and incubated 25 minutes on ice. The bacteria were then collected by centrifugation, and the pellet was gently resuspended with cold 0.1M $CaCl_2$ in $0.01 \times$ the original culture volume and incubated on ice for 20 hours.

EXAMPLE IV

In this example, isolation of two male-specific genomic clones is described.

To probe the 4000-clone genomic library described in Example III for male-specific clones, replica filters of the library were prepared as described in the next paragraph and then probed using the hybridization conditions defined in Example II.

The 4,000-colony library was lifted off the agar plates by placing a dry nitrocellulose filter on top of the colonies and gently peeling the filter, plus colonies, off the plate. The replica filter was made by placing a wet nitrocellulose filter onto the filter containing the colonies and gently pressing the two filters together. The filters were separated, and a third replica was made by again placing a wet nitrocellulose filter onto the original filter with colonies. After the filters were separated, they were placed on fresh $2 \times$ LB agar plates containing 15 µg/ml tetracycline. The plates containing the replicated filters were incubated at 37° C. until the colonies had regenerated. Two of the replicas were prepared for hybridization by lysing the colonies on the filters, neutralizing the filters, and baking them, as described below. The colonies on the filters were lysed by floating each filter on a 5 ml puddle of lysis buffer for 15 minutes. Each filter was then neutralized by transferring it to a 5 ml puddle of neutralizing buffer and allowing it to float for 15 minutes. The neutralization step was repeated once and the filters were then placed on absorbent paper towels and air dried for 30 minutes. The filters were then baked under vacuum in a vacuum oven at 70° C. for 2 hours.

Each of the two replica filters of the genomic library, prepared as described above, were probed under similar conditions as the Southern hybridization assay of Example II with the following modifications:

(1) The buffer with sheared herring sperm DNA, for prehybridization of filter with target DNA bound, contained a final concentration of 10% (w/v) dextran sulfate;

(2) The filters were removed from this 10% dextran sulfate-herring sperm DNA prehybridization buffer, lightly rubbed with a gloved hand while immersed in $5 \times$ SSPE to remove the cell debris, and then prehybridized with sonicated female bovine DNA as described in Example II, except that the Denhardt's solution was adjusted to $1 \times$; and (3) 2 μg of total bovine male DNA were nick-translated, to an average size of about 600 bp and $4.25 \times 10^8$ CPM/μg, following the procedure of Example II in a reaction volume of 300 μl, and used to make male-specific probe preparation, also as in Example II, that was then used for the hybridization.

15 positive colonies were thus identified.

From the third replica, these colonies and those near them were picked with a sterile toothpick into separate wells of a 96-well microtiter dish with each well containing 200 μl of 2× LB and 15 μg/ml tetracycline. For positive colonies closely spaced to other colonies, 8 colonies were picked and transferred to separate wells. For positive colonies well isolated from other colonies, 2 to 4 colonies were picked and transferred to separate wells. A total of 76 wells were inoculated. The microtiter dish was incubated at 37° C. until the media in the 76 wells became turbid. The bacteria in the wells were replica-plated onto nitrocellulose filters, which were placed on 2× LB agar plates containing 15 μg/ml tetracycline. Three replicas were made by placing a sterile device, with 96 metal prongs, designed to fit the microtiter dish, into the wells and then touching the device, with bacteria-containing drops of solution on 76 of the prongs, to the nitrocellulose filters. These filters, placed on the agar plates, were incubated at 37° C. until the colonies were 7 mm in diameter. The colonies on two of the filters were then prepared for hybridization as described above in this Example. One of these filters was then probed with 1 μg of nick-translated, bovine male specific probe preparation in the same manner as described above in this Example, including the steps for prehybridizating the filter. The other of these two filters was probed with nick-translated female bovine DNA as described in the next paragraph.

The hybridization of the filter with nick-translated female bovine DNA did not involve any solution hybridization between nick-translated female DNA with sonicated total bovine female DNA. The prehybridization of the filter with herring sperm DNA was as described in Example II. The filter was removed from the herring sperm DNA prehybridization and lightly rubbed with a gloved hand while immersed in 5× SSPE to remove cell debris. The filter was then prehybridized as described in Example II in the female bovine DNA prehybridization buffer with the omission of the total bovine female DNA. 1 μg of nick-translated total female DNA was prepared by the nick-translation procedure of Example II. The nick-translated female DNA was taken up in TE-buffer with 2.8 mg of sheared herring sperm DNA (average fragment size 500 bp), and the combined DNAs were ethanol precipitated and finally resuspended in 500 μl of deionized formamide. The DNA suspension was then placed in a boiling water bath for 3 minutes, and then transferred to 65° C. for 5 minutes. The resulting DNA solution was brought to a final volume of 1 ml consisting of, in addition to the DNA, 50% (v/v) deionized formamide, 1× Denhardt's solution, 5× SSPE, 10% (w/v) dextran sulfate, and 500 μg heparin. The solution was then filtered through nitrocellulose in a Sterifil Aspetic System 47 mm Apparatus (Millipore) and added directly to the bovine female DNA prehybridization buffer (including filter with DNA bound).

The post-hybridization washings and autoradiograph procedures employed with both probes were as described in Example II, except that the exposure of the filter probed with male DNA probe preparation was for 16 hours with an intensifying screen and the exposure of the filter probed with nick-translated female DNA was for 1.5 hours without an intensifying screen.

By comparing the intensities of the hybridization signals from the autoradiographs of the filters probed with male and female bovine DNA probes, respectively, 4 male-specific clones were identified.

These 4 clones were further characterized by isolating plasmid DNA and probing genomic Southern hybridization filters as described presently.

Plasmid DNA from each was isolated from 10 ml cultures following the quick boiling method described by Holmes and Quigley Anal. Biochem. 114, 193–197(1981), (also described in Bethesda Research Laboratories, Inc.'s Focus, volume 3 No. 2, page 4 (1981)), with some modifications as follows: Each clone was picked with a sterile toothpick and seeded into 10 ml of 2× LB containing 15 μg/ml tetracycline, and the culture was grown at 37° C. for 8 hours. Then chloramphenicol was added to a final concentration of 200 μg/ml and the culture was incubated at 37° C. for an additional 14 hours. The cells were then pelleted in a centrifuge tube and then resuspended, with vortex mixing in 700 μl of STET. The resuspended cells were then transferred to a siliconized 13×100 mm disposable glass test tube. 50 μl of stock lysozyme was added and the mixture was brought rapidly to a boil by placing the tube directly into a flame. Immediately after the boiling, the cell mass was transferred to a microfuge tube and centrifuged at 12,000×g for about 10 minutes at room temperature. The supernatant was removed by pipetting into a microfuge tube and mixed with an equal volume of cold isopropanol and held at −20° C. for 15 minutes. The precipitated DNA was pelleted by centrifugation, then resuspended in 100 μl TE-buffer and finally PCIA and CIA extracted as described in Example I. The aqueous phase (95 μl) was removed to another microfuge tube, the concentration of NaCl in the solution was brought to 0.25M and the DNA was then ethanol precipitated and finally resuspended in 10 μl of TE-buffer. 1 μl of each preparation was then nick-translated in a 15 μl nick-translation reaction mixture (Example II) to a The specific activity of $3.1 \times 10$ CPM/μg. The nick-translated product was chromatographed on a Sephadex G-50 column in TE-buffer as described in Example II, but using a 1 ml column instead of a 5 ml column. $1 \times 10^7$ CPM were added directly to the prehybridization buffer as described below.

Male and female bovine DNA (40 μg each), prepared as described in Example I, were digested with RsaI in separate tubes according to the manufacturer's instructions. Thereafter, 10 μg of digested DNA was loaded into each well of a 1% TBE agarose gel, with the male and female DNAs loaded in alternating lanes to produce 4 sets of lanes with male and female DNA in adjacent lanes. The DNA was electrophoresed through the argarose gel and a Southern hybridization filter prepared as described in Example II. After the filter was baked, it was cut into four equal filters, each containing one male and one female RsaI-digested sample of bovine chromosomal DNA.

Each of the four filters was probed with a different one of the nick-translated probes after prehybridization, as follows:

The filter was prehybridized in 5 ml of 50% (v/v) deionized formamide, 5× SSPE, 5× Denhardt's solution, 0.1% (w/v) SDS, and 200 μg/ml sheared and boiled herring sperm DNA. This prehybridization was carried out with incubation at 42° C. for 5 hours. The hybridization was then initiated by the addition of 64.5 μl (1×10$^7$ CPM total) of nick-translated plasmid probe in TE-buffer directly to the prehybridization solution (including the filter with DNA bound), yielding a final concentration of 2.0×10$^6$ CPM/ml. The hybridization was carried out at 42° C. for 17 hours. The conditions of temperature, pH, ionic strength and osmolality of the prehybridization step and hybridization step specified in this paragraph define "stringent conditions" for a prehybridization step and a hybridization step, respectively, as the term "stringent conditions" is used for such steps in the present specification.

As described in Example II, the filters were post-hybridization washed and exposed (for 2 hrs. 45 min. with intensifying screen) to X-Omat AR x-ray film. The conditions of temperature, pH, ionic strength and osmolality in this post-hybridization wash procedure define "stringent conditions" for post-hybridization washing, as the term "stringent conditions" is used for such washing in the present specification.

Unless it is clear from the context that the reference is to the hybridization step alone, reference in the present specification to "hybridization under stringent conditions" means prehybridization of the filter (with bound target DNA), hybridization, and post-hybridization washing under conditions, for each of the three steps, of temperature, pH, ionic strength and osmolality equivalent to "stringent conditions" for the step, as defined in the two preceding paragraphs.

The resulting autoradiographs indicate that two of the clones are male-specific. Both produced a range of positive hybridization signals from approximately 300 bp to approximately 6000 bp. There was complete absence of hybridization in the female lanes probed with either of these positive, male-specific clones. The two male-specific clones (cloned plasmids) have been designated pES5(2) and pES8.

EXAMPLE V

A preparative procedure for each plasmid, pES5(2) and pES8, and the characterization of their respective male-specific inserts, are described in this Example.

The plasmid-bearing E. coli LE392 was grown to an A$_{600}$ of 1.0 in 1× LB medium containing 15 μg/ml tetracyline. The plasmid copy number was then amplified by adding chloramphenicol to a final concentration of 200 μg/ml and incubating at 37° C. for 12 hours with vigorous shaking. The bacteria were then collected by centrifugation and washed by resuspending the bacterial pellet in ice-cold TEN buffer, and again collecting the cells by centrifugation. The bacterial pellet was then resuspended in ice-cold STE buffer. After the bacteria were resuspended, lysozyme stock was added to bring lysozyme to a concentration of 450 μg/ml. Lysis was achieved by then adding 5M NaCl to a concentration of 2.0M, followed by the addition of an equal volume of 0.2% (v/v) Triton X-100 and 40 mM EDTA, making a final NaCl concentration of 1.0M, and incubation of the preparation on ice for 30 minutes. Then the preparation was centrifuged in a Sorval SS-34 rotor (Maximum radius 0.7 cm, DuPont de Nemours, Inc., Wilmington, Del., U.S.A.) at 20,000 rpm (approximately 48,000×g) for 45 minutes. The supernatant was transferred to another tube and then extracted with PCIA followed by CIA, as described in Example I, third paragraph, and the DNA in the aqueous phase ethanol precipitated in the presence of 1M NaCl. The precipitated DNA, which includes the plasmid DNA, was resuspended in TE-buffer. As described in Example I, the DNA suspension was digested with heat-treated RNase A, PCIA and CIA extracted, and added to a centrifuge tube containing cesium chloride and ethidium bromide. The remainder of the preparative procedure is as described in Example I, except that two DNA bands form in the cesium chloride gradient formed in the 215,000×g, 18 hour centrifugation. The lower band, which is plasmid DNA, was collected into a centrifuge bottle and processed as described in Example I after the centrifugation step, with the resulting plasmid DNA finally resuspended in 400 μl of TE-buffer.

Each plasmid (3 μg) was digested with PstI according to the manufacturer's instructions and electrophoresed in a 1% TBE agarose gel as described in Example II. The DNA bands in the agarose gel were visualized by ethidium bromide staining according to a standard method, as described in Maniatis et al., supra, at page 161. The size of the insert fragments in pES5(2) and pES8 were estimated at 300 bp and 630 bp, respectively. These sizes include, of course, the (dG, dC) tails added to the fragments in order to ligate them into pBR322.

Two Southern hybridization filters, each containing 1 μg of PstI-digested pES5(2) and PstI-digested pES8 in adjacent lanes were prepared as described in Example II. One filter was probed with nick-translated pES5(2) and the other filter was probed with nick-translated pES8. These filters were probed using hybridization under stringent conditions. Under these conditions, the two inserts did not hybridize to each other and, therefore, there is no segment longer than about 10 bp in either plasmid which has a sequence identical to that of any segment in the other.

EXAMPLE VI

The number of bovine embryonic cells required for sex determination with both pES5(2) and pES8 together, and each plasmid separately, was estimated as follows: 60 nanograms each of male and female bovine chromosomal DNA, prepared as described in Example I, were resuspended separately in 2.4 ml TE-buffer to which were then added 240 μl of 3N NaOH. The alkaline DNA solutions were incubated at 65° C. for one hour. Following the incubation, the solutions were adjusted to 1M ammonium acetate by the addition of 2.64 ml of 2M ammonium acetate. From these stock solutions, various masses of DNA (5,000, 1,000, 500, 100, 50, 25, 10, and 5 picograms) were aliquoted to separate tubes and the volume of each tube was adjusted to 3.52 ml with a solution prepared by mixing 2.4 parts of TE-buffer with 0.24 parts 3M NaOH and 2.64 parts of 2M ammonium acetate. Seven solutions, each of 440 μl, of each concentration of DNA from each sex were prepared. Three of the seven were used in triplicate hybridizations with pES5(2) alone, three were used in triplicate hybridizations with pES8 alone, and the last was used in a single hybridization with pES5(2) and pES8 together. The solutions were applied to nitrocellulose filters using a Manifold II Slot Blotter apparatus according to the manufacturer's instructions. Prior to the application of the DNA, the nitrocellulose filters, and the blotter paper or Whatman 3 mm chromatography paper, used with the apparatus, were soaked briefly in 1M ammonium acetate. Following the application of DNA, the filters were removed from the Slot Blotter, air dried for 10 minutes, and baked under vacuum in a vacuum oven for 1 hour at 70° C. The filters were removed from the oven, and prehybridized, and then hybridized and post-hybridization washed according to the stringent conditions described in Example IV. The filters were hybridized for 17 hours with the following probes (at the following concentrations):
(1) pES5(2) alone ($1.5 \times 10^6$ CPM/ml);
(2) pES8 alone ($1.5 \times 10^6$ CPM/ml); and
(3) pES5(2) and pES8 together ($3.0 \times 10^6$ CPM/ml, each at $1.5 \times 10^6$ CPM/ml).

The specific activity of each probe was $4 \times 10^8$ CPM/µg. Each probe was prepared by nick-translating, by the procedure of Example II, 200 ng of plasmid (in a reaction mixture of 30 µl). The average size of nick-translated product was 600–1000 bp.

After elution from the Sephadex G-50 column, the concentration (in CPM/ml) of nick-translated probe (in TE-buffer) was measured, the probe solution was boiled for 3 minutes, and then an aliquot of the solution was added to the hybridization solution to bring the concentration of probe to the indicated concentration.

The autoradiographs resulting from hybridizing both probes together, prepared with a 24 hour film with intensifying screen, as described in Example II, show hybridization down to 25 picograms of male bovine DNA and no hybridization at any concentration studied to the female bovine DNA. 25 picograms of DNA is the amount of DNA that can be isolated from approximately 4 bovine cells. Hybridizations using the single plasmids alone detected less than 100 picograms of DNA (approximately 16 cells).

Thus, a probe including the bovine male-specific DNA of the PstI insert of pES5(2) and a probe including the bovine male-specific DNA of the PstI insert of pES8 can be used together to sex an embryo, with virtually 100% accuracy, using as few as 4 of the embryo's cells while preserving the remaining cells.

EXAMPLE VII

In this example, bovine embryonic tissue is used as a substrate for sex determination with pES5(2) and pES8. The experiment described in the example was performed to establish that pES5(2) and pES8 would produce a positive hybridization signal with bovine embryonic DNA, and that the intensity of a positive signal does not vary significantly between four equal portions of the same embryo.

A total of twenty embryos were prepared for sex determination. Ten of these embryos were processed as whole embryos and the remaining ten embryos were divided into four equal quarters and processed as quarter embryos. The embryonic cells, either whole embryos or quarter embryos, (100–120 cells or 25–30 cells, respectively) were individually transferred in a volume of 5 µl to a 500 µl microfuge tube containing 20 µl PK buffer. This resulted in a total of 50 microfuge tubes, ten of which contained whole embryos and forty of which contained quarter embryos. Proteinase K (2.5 µl of a 2 mg/ml H$_2$O stock) was added and the digestions were incubated at 22° C. for 15 minutes. The digestions were PCIA extracted as described in Example I and each aqueous phase was removed to a separate tube. PK buffer (20 µl) was added to the remaining PCIA and any residual DNA was extracted into the aqueous phase. This aqueous phase of each extraction was removed to the tube containing the aqueous phase for the first PCIA extraction, thus bringing the volume to approximately 40 µl. 3M NaOH stock (4 µl) was then added to each aqueous solution and the tubes were then incubated at 65° C. for 1 hour in order to denature the DNA in each sample. Following the denaturation, 2M ammonium acetate (50 µl) was added in order to neutralize each solution. The solutions were then applied to a nitrocellulose filter using a Manifold II Slot Blotter apparatus as described in Example VI. The filter was removed from the apparatus, air-dried, baked, prehybridized, and hybridized with nick-translated pES5(2) and pES8 together as described in Example VI. The filter was washed according to the stringent conditions described in Example IV.

The results of autoradiography (Example II) after a 68 hour exposure with an intensifying screen were as follows: 5 of the 10 slots containing whole embryos were strongly positive, and the remaining 5 slots containing whole embryos exhibited a complete absence of hybridization. Of the embryos divided into quarters, 6 of the 10 embryos produced a positive signal. For 5 of these 6, all four quarters gave a positive signal of approximately the same intensity. For the sixth, three of the quarters gave a positive signal of approximately the same intensity and one of the quarters did not give a positive signal. For 3 of the 4 quartered embryos that did not produce a positive signal, all four quarters did not. For the fourth, one of the quarters produced a positive signal and three did not.

The results show specific hybridization of the probes to bovine embryonic DNA with each quarter of an embryo producing a positive hybridization signal of equal intensity, thus indicating that the mass of DNA from the quarter of an embryo (approximately 25–30 cells) can be quantitatively recovered and probed for sex determination.

In the experiment described in this example, pES5(2) and pES8 were nick-translated with only one $^{32}$P-labeled deoxynucleoside triphosphate (see Example II). Those skilled in the art will understand that nick-translation of the plasmids with all four deoxynucleoside triphosphates labeled with $^{32}$P can result in a specific activity and sensitivity in the resulting probes at least about four times greater than the probes employed in the experiment. Thus, DNA from as few as about 6 embryonic cells can be probed for sex determination using the procedure of this example with pES5(2) and pES8 together, each nick-translated, with all four $^{32}$P-labeled deoxynucleoside triphosphates, to a specific activity of about $18 \times 10^8$ CPM/µg.

EXAMPLE VIII

The determination of the sex of bovine embryos is described in this Example.

A bovine embryo, advanced to a developmental stage conducive to embryo transfer, is obtained and a sample of embryonic tissue containing approximately 8 cells is removed from the embryo by a micromanipulation technique.

The DNA is extracted from the cells and affixed to a nitrocellulose filter, which is then prehybridized, hybridized with plasmids pES5(2) and pES8 together, that have been nick-translated to a specific acitivty of $4 \times 10^8$ CPM/µg, and post-hybridization washed. The pre-hybridization, hybridization and post-hybridization washes are under stringent conditions (See Example IV). As control, 50 picograms of DNA from each of a known bovine female and a known bovine male are treated the same as the DNA derived from the embryonic cells and also probed with the plasmids together, labeled to $4 \times 10^8$ CPM/μg and under stringent conditions. Autoradiographs of the three hybridizations are made as described in Example II.

A significantly stronger signal is obtained from hybridization with the embryo-derived DNA then with the female DNA, and it is concluded that the embryo is male.

The same procedure is carried out with another embryo taken at the stage of embryo transfer and with both pES5(2) and pES8. In this case, essentially no hybridization signal is obtained (i.e., the signals from probe recorded on the autoradiographs are essentially the same for embryo-derived and female-derived DNA). Thus, it is concluded that the embryo is a female.

The remaining embryonic cells that are not used in the sex-determining hybridization assays can undergo any of a number of procedures, known in the art, including, but not limited to:

(1) destruction, if the sex is not desired;
(2) reimplantation into a recipient cow, which is the natural or foster mother, for gestation to term;
(3) storage, as in freezing, for reimplanation at a time of choice; and
(4) manipulation to obtain a number of identical embryos which can be reimplanted, or stored for later implantation, to provide multiple identical individuals.

EXAMPLE IX pES5(2) and pES8 can be used to sex a fetus or embryo of any individual of genus Bos.

Male and female bovine total DNA was prepared from the Holstein and Hereford breeds by a modification of the procedure described in Example I: 500 mg of liver tissue from each sex of each breed was homogenized separately in 500 μl of PK buffer. Proteinase K was added to the tissue/buffer solution at a final concentration of 200 μg/ml and the mixture was incubated at room temperature for 30 minutes. The DNA preparation was then PCIA extracted and then CIA extracted, and finally the DNA was ethanol precipitated from the aqueous phase. The precipitate was resuspended in 100 μl TE-buffer. Heat-treated RNase A is then added to a final concentration of 50 μg/ml. The RNase A digestion was carried out at 37° C. for 15 minutes and the resulting solution PCIA extracted and then CIA extracted and the DNA again ethanol precipitated. The DNA was resuspended in TE-buffer.

The concentration of DNA in the preparations was determined, as in Example I, by UV absorbance, and 100 ng of each of the DNA's was applied to a nitrocellulose filter using a Manifold II Slot Blotter apparatus as described in Example VI. The nitrocellulose filter was baked, prehybridized, hybridized, and washed using the stringent conditions described in Example IV. The hybridization was with nick-translated pES5(2) and pES8 together as in Example VI and the autoradiography was also carried out as described in Example VI. With both breeds, the results indicated that pES5(2) and pES8 in combination are male-specific and useful for sexing.

EXAMPLE X

Following the procedures of Example IX, male and female chromosomal DNA from swine and sheep were analyzed. The results indicate that pES5 (2) and pES8 are specific for male DNA of species of genus Bos, as no hybridization was observed with any of the swine or sheep DNA.

DEFINITIONS AND DETAILS

In the following, additional information is provided on various reagents, enzymes, solutions, buffers, media, equipment and other items referred to, as well as various abbreviations used, in the present specification:

| | |
|---|---|
| Agar | Difco Laboratories<br>Detroit, Michigan, U.S.A. |
| Agarose | Bio-Rad, Inc.<br>Chemical Division<br>Richmond, California, U.S.A. |
| Bacto-tryptone and<br>Bacto-yeast extract | Difco Laboratories<br>Detroit, Michigan, U.S.A. |
| Bio-Gel P-60 | Bio-Rad, Inc.<br>Chemical Division<br>Richmond, California, U.S.A. |
| Bovine Serum<br>Albumin | Sigma Chemical Co.<br>St. Louis, Missouri, U.S.A.<br>Catalog No. A2153;<br>Fraction V, powder |
| CPM | Counts per minute, as<br>measured on a Beckman LS7800<br>liquid scintillation counter<br>on the $^{32}P$ channel<br>(Beckmann Instruments, Inc.,<br>Fullerton, California, U.S.A.) |
| Chloramphenicol | Sigma Chemical Co.<br>St. Louis, Missouri, U.S.A.<br>Catalog No. C-0378 |
| CIA | 96% (v/v) chloroform, 4%<br>(v/v) isoamyl alcohol |
| Deionized Formamide | 50 ml formamide are mixed<br>with 5 g of mixed-bed ion<br>exchange resin (AG 501-X8,<br>20–50 mesh,<br>catalog no. 142-6424,<br>Bio-Rad Laboratories,<br>Richmond, California, U.S.A.)<br>and the mixture stirred for<br>30 min. at room temperature<br>and then filtered through<br>Whatman No. 1 filter paper.<br>Stored at −20° C. |
| 50X Denhardt's<br>Solution | 5 g Ficoll 400 (Pharmacia, Inc.,<br>Piscataway, New Jersey, USA,<br>catalog No. 17-0400-01,<br>average molecular weight<br>approx. 400,000 daltons)<br>5 g polyvinylpyrrolidone<br>PVP-360 (Sigma Chemical Co.,<br>St. Louis, Missouri, USA,<br>average molecular weight<br>approx. 360,000 daltons)<br>5 g bovine serum albumin;<br>add $H_2O$ to 500 ml. |
| Deoxynucleoside<br>Triphosphates | Sigma Chemical Company, Inc.<br>St. Louis, Missouri, U.S.A. |
| Deoxynucleoside<br>Triphosphates<br>(alpha-$^{32}P$-labeled) | New England Nuclear, Inc.<br>Boston, Massachusetts, U.S.A. |
| Dextran Sulphate | Pharmacia, Inc.<br>Piscataway, New Jersey, U.S.A.<br>Catalog No. 17-0340-01<br>Ave. mol. wt. approximately<br>500,000 d<br>Sodium salt. |
| DNaseI | Sigma Chemical Co.<br>St. Louis, Missouri, U.S.A.<br>Catalog No. D4763<br>(type I, bovine pancreatic) |
| DNase Stock | 0.1 ug/ml of DNase I in<br>100 mM potassium phosphate<br>buffer (pH 7.0),<br>10 mM of 2-mercaptoethanol,<br>50% (v/v) glycerol |
| 10X dNTP mix | 200 uM each of dGTP,<br>dATP and dTTP in<br>20 mM Tris (pH 7.4) |
| E. coli DNA<br>Polymerase I | New England Biolabs, Inc.<br>Beverly, Massachusetts, U.S.A.<br>Catalog No. 209 |

| | |
|---|---|
| | (supplied in 0.1 M potassium phosphate buffer (pH 6.5), 1.0 mM dithiothreitol and 50% (v/v) glycerol). 5000–15,000 units/ml is the amount of enzyme required to incorporate 10 nmole of total nucleotide into acid-precipitable form in 30 min. at 37° C. |
| Elutip-d Column | An ion-exchange column for rapid purification and concentration of DNA. Schleicher and Schuell, Inc. Keene, New Hampshire, U.S.A. |
| dGMP-tailed pBR322 | New England Nuclear, Inc. Boston, Massachusetts, U.S.A. The pBR322 is linearized with PstI at the single PstI site in the bla gene on the plasmid and the ends of the linearized plasmid are tailed with approximately 10 to 20 dGMP residues at each end using essentially the same procedure described above for tailing DNA fragments with dCMP residues. |
| Heparin | Sigma Chemical Co. St. Louis, Missouri, U.S.A. Catalog No. H-7005 Grade 2, porcine intestinal mucosal, Na-salt |
| Herring sperm DNA | Sigma Chemical Co. St. Louis, Missouri, U.S.A. Catalog No. D-1632 Type VII, Sodium salt |
| Herring testes DNA | Sigma Chemical Co. St. Louis, Missouri, U.S.A. Catalog No. D-6898 |
| Lambda Phage and PhiX174 DNA for Sizing | New England Biolabs, Inc. Beverly, Massachusetts, U.S.A. Lambda (Hind III), catalog no. 301-2 PhiX174 (Hae III), catalog no. 302-6 |
| 2X LB | 10 g Bacto-tryptone 10 g Bacto-yeast extract 5 g NaCl adjusted to 1 liter with $H_2O$ autoclaved |
| 2X LB Agar with 15 ug/ml tetracycline | Mix 1.5% (w/v) agar with 2X LB; autoclave, when cooled to 50° C., add tetracycline solution to tetracycline concentration of 15 ug/ml; pour into plates for setting |
| Lysis Buffer | 1.5 M NaCl 0.5 M NaOH |
| Lysozyme Stock | Lysozyme (Sigma Chemical Co., St. Louis, Missouri, U.S.A. Catalog No. L-6876, Grade 1) at 10 mg/ml in $H_2O$ |
| Manifold II Slot Blotter | Schleicher and Schuell, Inc. Keene, New Hampshire, U.S.A. In place of blotter paper supplied for the machine by Schleicher and Schuell, Whatman 3 mm chromatography paper can be used. |
| Neutralizing Buffer | 1.5 M NaCl 0.5 M Tris-Cl (pH 7.4) |
| 10X Nick-Translation Buffer | 0.5 M Tris-Cl (pH 7.2) 0.1 M $MgSO_4$ 1 mM dithiothreitol 50 ug/ml bovine serum albumin |
| Nitrocellulose Filters | Schleicher and Schuell, Inc. Keene, New Hampshire, U.S.A. Type BA85 |
| PCIA | 50% (v/v) phenol, 48% (w/v) chloroform, 2% (v/v) isoamylalcohol |
| PK Buffer | 0.14 M NaCl 0.05 M Tris (pH 8.4) 1% (w/v) SDS 0.01 M EDTA |
| Proteinase K | Boehringer Mannheim Biochemicals, Inc. Indianapolis, IN, U.S.A. Catalog No. 745-723 |
| Restriction Enzymes | New England Biolabs, Inc. Beverly, Massachusetts, U.S.A. |
| Ribonuclease A | Sigma Chemical Co. St. Louis, Missouri, U.S.A. Catalog No. R-5250 Type X-A |
| Sephadex G-50 | Pharmacia, Inc. Piscataway, New Jersey, U.S.A. Catalog No. 17-0042-01 |
| 20X SSPE | 3.6 M NaCl 0.16 M NaOH 0.2 M $NaH_2PO_4$—$H_2O$ 0.02 M EDTA adjust pH to 7.0 with NaOH |
| STE Buffer | 25% (w/v) sucrose 50 mM Tris-Cl (pH 7.4) 20 mM EDTA |
| STET Buffer | 8% (w/v) sucrose 5% (v/v) Triton X-100 50 mM EDTA 50 mM Tris-Cl (pH 8.0) |
| TBE agarose gel | Agarose gel prepared with agarose at a specified (w/v) percentage in 1X TBE buffer |
| 1X TBE Buffer | 0.089 M Tris 0.089 M boric acid 0.002 M EDTA pH 7.7 |
| TE-buffer | 10 mM Tris (pH 7.4) 1 mM EDTA |
| TEN buffer | 0.8% (w/v) NaCl 20 mM Tris (pH 8.0) 20 mM EDTA |
| Terminal Transferase (Calf thymus) | Ratliff Biochemicals Los Alamos, New Mexico, U.S.A; or Boehringer-Mannheim Biochemicals, Inc. Indianapolis, Indiana, U.S.A. Catalog No. 604-100. |
| 5X Terminal Transferase Buffer | 1 M $KAs(CH_3)_2O_2$ 5 mM $CoCl_2$ 10 mM beta-mercaptoethanol pH 7.2 |
| Tetracycline Solution | 15 mg crystalline tetracycline (acid form) (Sigma Chemical Co., St. Louis, Missouri, U.S.A., catalog no. T-3258) per ml methanol. |
| ug | microgram |
| ul | microliter |

DEPOSITS

Viable cultures of *E. coli* LE392 (pES5(2)) and *E. coli* LE392 (pES8) have been deposited at the American Type Culture Collection (ATCC), Rockville, Md., U.S.A., under the terms of the Budapest Treaty on the International Recognition of the Deposit of Microorganisms for Purposes of Patent Procedure and the Regulations promulgated thereunder. Samples of said deposits are and will be available to industrial property offices and other parties legally entitled to receive them under said Treaty and Regulations.

the ATCC deposit number of *E. coli* LE392 (pES5 (2)) is 53098.

The ATCC deposit number of *E. coli* LE392 (pES8) is 53099.

As those of skill will recognize, *E. coli* LE392 free of pES5(2) and pES8 can be obtained by curing *E. coli* LE392 (pES5(2)) or *E. coli* LE392 (pES8) of plasmid. This can be accomplished by culturing either strain in the absence of tetracycline.

While the present invention has been described herein with reference to specific examples, numerous variations and modifications will be apparent to those skilled in the art. These modifications and variations are within the scope of the invention described and claimed herein.

What is claimed is:

1. A labeled or unlabeled single stranded nucleic acid which comprises:
    (a) a segment which has substantially the same sequence as that of either strand of a fragment selected from the group consisting of:
       (1) the smaller PstI fragment of plasmid pES5(2),
       (2) the smaller PstI fragment of plasmid pES8,
       (3) the 5–6 kbp RsaI fragment of total male Holstein DNA, and
       (4) the 4 kbp RsaI-EcoRI fragment of total male Holstein DNA; or
    (b) any segment, more than 20 bp in length, of any of the segments of subparagraph (a) of this claim;
    provided that said single stranded nucleic acid hybridizes to a significantly greater extent with total DNA of males of a breed of a species of genus Bos than with total DNA of females of the breed.

2. A nucleic acid according to claim 1 which is radioactively labeled with $^3H$ or $^{32}P$.

3. A nucleic acid according to claim 1 which is non-radioactively labeled with biotin.

4. A nucleic acid according to claim 1 which, under stringent conditions, hybridizes to a significantly greater extent with total DNA of males of a breed selected from the group consisting of Hereford and Holstein than with total DNA of females of the breed.

5. A nucleic acid according to claim 4 which is radioactively labeled with $^3H$ or $^{32}P$.

6. A nucleic acid according to claim 4 which is non-radioactively labeled with biotin.

7. A nucleic acid according to claim 4 which is DNA.

8. A nucleic acid according to claim 7 which is radioactively labeled with $^3H$ or $^{32}P$.

9. A nucleic acid according to claim 7 which is non-radioactively labeled with biotin.

10. A DNA according to claim 7 which has substantially the same sequence as that of either strand of a DNA selected from the group consisting of closed circular pES5(2), linearized pES5(2), closed circular pES8, linearized pES8, the smaller PstI fragment of pES5(2), and the smaller PstI fragment of PES8.

11. A DNA according to claim 10 which is radioactively labeled with $^3H$ or $^{32}p$.

12. A DNA according to claim 10 which is non-radioactively labeled with biotin.

13. A DNA according to claim 10 which is either strand of a DNA selected from the group consisting of closed circular and linearized pES5(2), closed circular and linearized pES8, the smaller PstI fragment of pES5(2), and the smaller PstI fragment of pES8.

14. A DNA according to claim 13 which is radioactively labeled with $^3H$ or $^{32}p$.

15. A DNA according to claim 13 which is non-radioactively labeled with biotin.

16. A method of sexing an embryo or fetus of a species of genus Bos which comprises:

(i) contacting the DNA of cells of said embryo or fetus under hybridization conditions with one or more hybridization probes, each of which is a detectably labeled, single-stranded nucleic acid which comprises:
        (a) a segment which has substantially the same sequence as that of either strand of a fragment selected from the group consisting of:
           (1) the smaller PstI fragment of plsmid pES5(2),
           (2) the smaller PstI fragment of plasmid pES8,
           (3) the 5–6 kbp RsaI fragment of total male Holstein DNA, and
           (4) the 4 kbp RsaI-EcoRI fragment of total male Holstein DNA; or
        (b) any segment, more than 20 bp in length, of any of the segments of subparagraph (i)(a) of this claim;
        provided that at least one of said single stranded nucleic acids, under the hybridization conditions, hybridizes to a significantly greater extent with total DNA of males of a breed of a species of the genus Bos than with total DNA of females of the breed; and
    (ii) ascertaining whether significant hybridization occurs between the DNA of the cells of the embryo or fetus and the hydridization probe or probes.

17. A method according claim 16 wherein one or more of the hybridization probes is a nucleic acid which is non-radioactively labeled with biotin and wherein each of the probes is a nucleic acid which hybridizes under stringent conditions to a significantly geater extent with total DNA of males of a breed selected from the group consisting of Hereford and Holstein than with total DNA of females of the breed.

18. A method according to claim 16 wherein each of the hybridization proves is a nucelic acid which is radioactively labeled with $^{32}P$ or $^3H$ and which hybridizes under stringent conditions to a significantly greater extend with total DNA of males of a breed selected from the group consisting of Hereford and Holstein than total DNA of females of the breed.

19. A method according to claim 18 wherein each of the hybridization probes is a DNA and is obtained by denaturing DNA made by nick-translation of a DNA with a sequence which is substantially the same as that of a DNA seleted from the group consisting of closed circular pES5(2), closed circular pES8, linearized pES5(2), linearized pES8, the smaller PStI fragment of pES5(2) and the smaller PstI fragment of PES8.

20. A method according to claim 19 wherein each of the hybridization probes is obtained by denaturing DNA made by nick-translation, with one or more of the $^{32}p$-labeled deoxynucleoside triphosphates, of a plasmid selected from the group consisting of pES5(2) and pES8.

21. A method according to claim 20 wherein the DNA probed is derived from 4 to 8 embryonic cells, the hybridization probes are obtained by nick-translation of pES5(2) and pES8 with all four deoxynucleoside tirphosphates labeled with $^{32}P$, the specific activity of the probes is between about $16 \times 10^8$ and about $20 \times 10^8$ CPM/$\mu$g, and the activity of probes derived from pES5 (2) in the hybridization with the embryonic DNA is between about 0.67 and about 1.5 times that of probes derived from pES8.

22. A doube-stranded DNA which has substantially the same sequence as a DNA selected from the group consisting of closed circular and linarized pES5(2), closed circular and linearized pES8, the smaller PstI fragment of pES5(2), and the smaller PstI fragment of pES8.

23. A nucleic acid according to claim 22 which is radioactively labeled with $^3$H or $^{32}$P.

24. A nucleic acid according to claim 22 which is non-radioactively labeled with biotin.

25. A DNA according to claim 22 which is a DNA selected from the group consisting of closed circular and linearized pES5(2), closed circular and linearized pES8, the smaller PstI fragment of pES5(2), and the smaller PstI framgent of pES8.

26. A nucleic acid according to claim 25 which is radioactively labeled with $^3$H or $^{32}$P.

27. A nucleic acid according to claim 25 which is non-radioactively labeled with biotin.

* * * * *

UNITED STATES PATENT AND TRADEMARK OFFICE
CERTIFICATE OF CORRECTION

PATENT NO. : 4,769,319
DATED : September 6, 1988
INVENTOR(S) : S. Ellis and M. Harpold It is certified that error appears in the above-identified patent and that said Letters Patent is hereby corrected as shown below:

| | |
|---|---|
| Column 3, Line 29: | After "hybridization" delete --;--. |
| Column 13, Line 66: | Change "E.-coli" to --E. coli--. |
| Column 16, Line 43: | After "a" delete "The". |
| Column 16, Line 43: | Change "10" to --$10^8$--. |
| Column 17, Line 62: | Change "0.7" to --10.7--. |
| Column 24, Line 65: | Change "the" to --The--. |
| Column 25, Line 13: | Change "single stranded" to --single-stranded--. |
| Column 25, Line 26: | Change "single stranded" to --single-stranded--. |
| Column 26, Line 9: | Change "plsmid" to --plasmid--. |
| Column 26, Line 17: | Change "single stranded" to --single-stranded--. |
| Column 26, Line 31: | Change "geater" to --greater--. |
| Column 26, Line 36: | Change "proves" to --probes--. |
| Column 26, Line 39: | Change "extend" to --extent--. |
| Column 26, Line 41: | After "than" insert --with--. |

UNITED STATES PATENT AND TRADEMARK OFFICE
CERTIFICATE OF CORRECTION

PATENT NO. : 4,769,319

DATED : September 6, 1988

INVENTOR(S) : S. Ellis and M. Harpold

It is certified that error appears in the above-identified patent and that said Letters Patent is hereby corrected as shown below:

Column 26, Line 46: Change "seleted" to --selected--.

Column 26, Line 49: Change "PES8" to --pES8--.

Column 26, Line 53: Change "$^{32}p$" to --$^{32}P$--.

Column 26, Line 59-60: Change "tirphosphates" to --triphosphates--.

Signed and Sealed this

Fourth Day of April, 1989

Attest:

DONALD J. QUIGG

*Attesting Officer*      *Commissioner of Patents and Trademarks*